US012709732B2

(12) United States Patent
Wei et al.

(10) Patent No.: US 12,709,732 B2
(45) Date of Patent: Aug. 18, 2026

(54) USE OF HYALURONIC ACID OR SALT THEREOF AND/OR TREHALOSE IN STABILIZING ERGOTHIONEINE, AND ERGOTHIONEINE COMPOSITION CONTAINING HYALURONIC ACID OR SALT THEREOF AND/OR TREHALOSE

(71) Applicants: BLOOMAGE BIOTECHNOLOGY CORPORATION LIMITED, Shandong (CN); BLOOMAGE BIOTECH (TIANJIN) CO., LTD., Tianjin (CN)

(72) Inventors: Yujie Wei, Shandong (CN); Zhen Lu, Shandong (CN); Qingping Chen, Shandong (CN); Jie Li, Shandong (CN); Yuanjun Sun, Shandong (CN); Wenjuan Xie, Shandong (CN); Ranran Du, Shandong (CN); Wenyi Guo, Shandong (CN); Xueping Guo, Shandong (CN)

(73) Assignees: BLOOMAGE BIOTECHNOLOGY CORPORATION LIMITED, Shandong (CN); BLOOMAGE BIOTECH (TIANJIN) CO. LTD., Tianjin (CN)

( * ) Notice: Subject to any disclaimer, the term of this patent is extended or adjusted under 35 U.S.C. 154(b) by 454 days.

(21) Appl. No.: 18/036,257

(22) PCT Filed: Nov. 9, 2021

(86) PCT No.: PCT/CN2021/129504
§ 371 (c)(1),
(2) Date: May 10, 2023

(87) PCT Pub. No.: WO2022/100567
PCT Pub. Date: May 19, 2022

(65) Prior Publication Data

US 2023/0407238 A1 Dec. 21, 2023

(30) Foreign Application Priority Data

Nov. 10, 2020 (CN) ......................... 202011249538.8

(51) Int. Cl.
*A61K 9/16* (2006.01)
*C12N 1/14* (2026.01)

(52) U.S. Cl.
CPC ............ *C12N 1/14* (2013.01); *C12N 2500/34* (2013.01)

(58) Field of Classification Search
CPC .................................................... A61K 9/1652
See application file for complete search history.

(56) References Cited

U.S. PATENT DOCUMENTS

2016/0120781 A1* 5/2016 Powell .................... A61P 43/00 424/617

FOREIGN PATENT DOCUMENTS

| | | |
|---|---|---|
| CN | 103181933 | 7/2013 |
| CN | 107114355 | 9/2017 |
| CN | 109938332 | 6/2019 |
| CN | 110283856 | 9/2019 |
| CN | 110327242 | 10/2019 |
| CN | 110522671 | 12/2019 |
| CN | 111265420 | 6/2020 |
| CN | 111557875 | 8/2020 |
| CN | 112353800 | 2/2021 |
| KR | 101238968 | 3/2013 |
| KR | 10-2018-0118409 | 10/2018 |

OTHER PUBLICATIONS

Essendoubi M, Gobinet C, Reynaud R, Angiboust JF, Manfait M, Piot O. Human skin penetration of hyaluronic acid of different molecular weights as probed by Raman spectroscopy. Skin Res Technol. Feb. 2016;22(1):55-62. doi: 10.1111/srt.12228. Epub Apr. 16, 2015. PMID: 25877232. (Year: 2016).*

Mintel, anonymous: "Plump & Prime Luxury Face Plumping Primer Serum", XP093140056, Database accession No. 8179403, Oct. 8, 2020.

Mintel, anonymous: "Hydrating Lotion", XP093140069, Database accession No. 7823551, Jun. 10, 2020.

Mintel, anonymous: "Repair Lotion", XP0931400 base accession No. 7816793, Jul. 9, 2020.

Extended European Search Report issned Mar. 26, 2024 in corresponding European Patent Application No. 21891087.5.

International Search Report issued Jan. 27, 2022 in International (PCT) Application No. PCT/CN2021/129504.

(Continued)

*Primary Examiner* — Ruth A Davis

(74) *Attorney, Agent, or Firm* — Wenderoth, Lind & Ponack, L.L.P.

(57) ABSTRACT

The present application provides a use of a hyaluronic acid or a salt thereof and/or trehalose in stabilizing ergothioneine, an additive for stabilizing ergothioneine, the additive containing the hyaluronic acid or the salt thereof and/or trehalose, and a composition, the composition containing ergothioneine, the hyaluronic acid or the salt thereof, and trehalose. Compared with other auxiliary materials, the hyaluronic acid or the salt thereof and trehalose provided by the present invention can obviously mitigate the damage of a high temperature to ergothioneine, thereby increasing the yield of an ergothioneine powder product. The composition obtained by the present invention has good antioxidant and anti-apoptotic effects. Moreover, the inhibitory and scavenging effects of a composition obtained by compounding the hyaluronic acid or the salt thereof and trehalose to be used as an auxiliary material on intracellular reactive oxygen species are obviously better than those of a composition obtained by using a single hyaluronic acid or a salt thereof or trehalose as an auxiliary material.

10 Claims, No Drawings

(56) References Cited

OTHER PUBLICATIONS

Wang et al., "Antioxidant activity of ergothioneine from king oyster mushrooms and effects of environment on its stability"; Food and Fermentation Industries, vol. 45, No. 14, Mar. 27, 2019, pp. 47-56.

* cited by examiner

USE OF HYALURONIC ACID OR SALT THEREOF AND/OR TREHALOSE IN STABILIZING ERGOTHIONEINE, AND ERGOTHIONEINE COMPOSITION CONTAINING HYALURONIC ACID OR SALT THEREOF AND/OR TREHALOSE

FIELD OF THE APPLICATION

This application relates to the technical field of biochemical industry, particularly to the use of hyaluronic acid or a salt thereof and/or trehalose in stabilizing ergothioneine, and ergothioneine composition containing hyaluronic acid or a salt thereof and/or trehalose.

BACKGROUND OF THE APPLICATION

Ergothioneine (2-mercaptohistidine trimethylbetaine) is a rare amino acid with antioxidant, UV protection and cell repair properties. Ergothioneine exists in many animals and plants, and cannot be synthesized by the animal body itself, and can only be ingested from food. There are three methods for preparing ergothioneine: chemical synthesis, extraction and microbial fermentation. Due to the problems of high cost and unsafety in the preparation of ergothioneine by chemical synthesis and extraction methods, the preparation of ergothioneine products by microbial fermentation has attracted more and more attention.

When ergothioneine is produced by microbial fermentation, the drying of ergothioneine fermentation broth is usually spray-drying. Spray-drying is a drying method that sprays the material liquid into mist droplets and disperses them in high temperature, so that the moisture contained in the feed liquid evaporates quickly. It has the characteristics of fast heat transfer, rapid water evaporation and short drying time, and the product quality is good, the texture is crunchy, and the dissolution performance is also good, which can improve the dissolution rate of some preparations. Common auxiliary materials for spray-drying are dextrin, β-cyclodextrin, soluble starch, micropowder silica gel, microcrystalline cellulose, lactose, and maltodextrin. When ergothioneine is dried by the existing spray-drying method, ergothioneine is easily damaged, which affects the yield of the powder product obtained by drying ergothioneine.

CONTENT OF THE APPLICATION

In order to solve the problems in the prior art, the present application provides the use of hyaluronic acid or a salt thereof and/or trehalose in stabilizing ergothioneine, an additive for stabilizing ergothioneine, and a composition. The technical scheme of the present application is as follows:

1. Use of hyaluronic acid or a salt thereof and/or trehalose for stabilizing ergothioneine.
2. The use according to item 1, wherein the hyaluronic acid or a salt thereof and/or trehalose is used to improve the thermostability of ergothioneine.
3. The use according to item 1, wherein the molecular weight of the hyaluronic acid or a salt thereof is 3 KDa to 30 KDa, preferably 3 KDa to 10 KDa.
4. An additive for stabilizing ergothioneine, wherein the additive comprises hyaluronic acid or a salt thereof and/or trehalose.
5. The additive according to item 4, wherein the additive comprises hyaluronic acid or a salt thereof and trehalose, and the mass ratio of the hyaluronic acid or a salt thereof to trehalose is 1:99 to 50:50, preferably 1:19 to 1:10.
6. The additive according to item 4, wherein the molecular weight of the hyaluronic acid or a salt thereof is 3 KDa to 30 KDa, preferably 3 KDa to 10 KDa.
7. The additive according to item 4, wherein, the additive is used as an auxiliary material for spray-drying ergothioneine fermentation broth.
8. A composition, wherein the composition comprises ergothioneine, hyaluronic acid or a salt thereof and trehalose.
9. The composition according to item 8, wherein, in parts by weight, ergothioneine is 1 part by weight, hyaluronic acid or the a salt thereof is 20 to 1000 parts by weight, preferably 100 to 180 parts by weight, and trehalose is 1000 to 1980 parts by weight, preferably 1800 to 1900 parts by weight.
10. The composition according to item 8, wherein the molecular weight of the hyaluronic acid or a salt thereof is 3 KDa to 30 KDa, preferably 3 KDa to 10 KDa.
11. The composition according to item 8, wherein the composition has an antioxidant effect. Compared with other auxiliary materials, the hyaluronic acid or a salt thereof and trehalose provided by the present application can obviously alleviate the damage to ergothioneine caused by high temperature, and improve the yield of ergothioneine powder products. The composition obtained by the application has better antioxidative effect and antiapoptotic effect. The inhibitory and scavenging effects on intracellular reactive oxygen species of the composition obtained by simultaneously using hyaluronic acid or a salt thereof and trehalose as auxiliary materials are significantly higher than that of single hyaluronic acid or a salt thereof or trehalose as auxiliary materials.

DETAILED DESCRIPTION OF THE APPLICATION

Unless otherwise defined, related technical and scientific terms in this specification have the same meaning as commonly understood by those of ordinary skill in the art. Although methods and materials similar or identical to those described herein can be used in experiments or practical applications, the materials and methods are described below. In case of conflict, the present specification, including definitions therein, will control, and otherwise, the materials, methods and examples are illustrative and not restrictive. The present application will be further described below with reference to specific examples, but it is not intended to limit the scope of the present application.

The experimental methods used below are conventional methods unless otherwise required.

The materials and reagents used below can be obtained from commercial sources unless otherwise specified.

Matsutake is preferably *Tricholoma matsutake* SR-LY, which has been preserved in the China Center for Type Culture Collection (CCTCC) in Wuhan University (zip code 430072), Wuhan, China on Oct. 16, 2020. The preservation number is CCTCC No: M 2020587.

*Hericium erinaceus* is preferably *Hericium erinaceus* with a preservation number of CCTCC No: M 2018567, which has been preserved in the China Center for Type Culture Collection (CCTCC) in Wuhan University, Wuhan, China (zip code 430072) on Aug. 23, 2018.

The spray-drying equipment is a centrifugal or pressure spray dryer.

The present application provides use of hyaluronic acid or a salt thereof and/or trehalose in stabilizing ergothioneine.

Hyaluronic Acid (HA) is a natural mucopolysaccharide formed from alternating units of D-glucuronic acid and N-acetylglucosamine in a linear chain. Hyaluronic acid shows a variety of important physiological functions in the body with its unique molecular structure and physicochemical properties. Most importantly, it has a special water-retaining effect and is the best moisturizing substance found in nature, and is known as an ideal natural moisturizing factor (NMF). Moreover, the hyaluronic acid molecule is in the shape of a rigid helical column in space. The inner side of the column has strong water absorption due to the presence of a large number of hydroxyl groups. On the other hand, due to the continuous orientation of the hydroxyl groups, a hydrophobic area is formed on the hyaluronic acid molecular chain, so that hyaluronic acid can form a three-dimensional network structure.

Trehalose is formed by the condensation of two glucose molecules through a hemiacetal hydroxyl group. Since there is no free aldehyde group, it is a non-reducing disaccharide. The molecular formula is $C_{12}H_{22}O_{11}$ (containing two crystal waters). Since two glucose molecules can form α-glucopyranose and β-glucopyranose, three isomers can be obtained through α-1,1glycosidic linkage: trehalose (α, α), isotrehalose (β, α) β) and neotrehalose (α, β). Because trehalose has unique biological functions, it can effectively maintain the stability and integrity of intracellular biological membrane, proteins and active peptides under adversity. It is praised as the sugar of life and can be widely used in biological preparations, medicament, food, health products, fine chemicals, cosmetics, feed and agricultural science and other industries.

In a specific embodiment, the hyaluronic acid or a salt thereof and/or trehalose is used to improve the thermostability of ergothioneine. Wherein, the salt of hyaluronic acid is at least one selected from the group consisting of: sodium salt, potassium salt, magnesium salt, zinc salt, calcium salt or quaternary ammonium salt.

Ergothioneine (2-mercaptohistidine trimethylbetaine) is a rare amino acid with antioxidant, UV protection and cell repair properties. Ergothioneine exists in many animals and plants, and cannot be synthesized by the animal body itself, and can only be ingested from food.

When ergothioneine is produced by microbial fermentation, the drying of ergothioneine fermentation broth is usually by spray-drying. Among them, spray-drying is a drying method in which the material liquid is sprayed into mist droplets and dispersed in high temperature, so that the moisture contained in the feed liquid can be quickly evaporated. It has the characteristics of fast heat transfer, rapid water evaporation and short drying time, and the product quality is good, the texture is crunchy, the solubility is also good, and the dissolution rate of some preparations can be improved. However, ergothioneine is easily damaged at high temperature, which finally affects the yield of the ergothioneine powder obtained by drying.

The present application provides an additive for stabilizing ergothioneine, wherein the additive comprises hyaluronic acid or a salt thereof and/or trehalose. That is, the additive may be hyaluronic acid or a salt thereof, trehalose, or a combination of hyaluronic acid or a salt thereof and trehalose in any proportion. Wherein, the salt of hyaluronic acid is at least one selected from the group consisting of: sodium salt, potassium salt, magnesium salt, zinc salt, calcium salt or quaternary ammonium salt.

In a specific embodiment, the additive comprises hyaluronic acid or a salt thereof and trehalose. The mass ratio of the hyaluronic acid or a salt thereof to trehalose is 1:99 to 50:50, such as 1:99, 1:90, 1:80, 1:70, 1:60, 1:50, 1:40, 1:30, 1:20, 1:19, 1:10, preferably 1:19 to 1:10.

In a specific embodiment, the molecular weight of hyaluronic acid or a salt thereof in the additive is 3 KDa to 30 KDa, for example, it can be 3 KDa, 5 KDa, 10 KDa, 15 KDa, 20 KDa, 25 KDa, 30 KDa, preferably 3 KDa to 10 KDa.

In a specific embodiment, the additive is used as an auxiliary material for spray-drying treatment of ergothioneine fermentation broth. Wherein, the ergothioneine fermentation broth can be the fermentation broth of any existing microorganisms in the prior art. For example, ergothioneine fermentation broth of matsutake, *Hericium erinaceus*, etc.

Preferably, the spray is centrifugal or pressure spray-drying, the air inlet temperature is 150° C. to 200° C., and the air outlet temperature is 50° C. to 100° C.

Preferably, 1 to 30% (w/v, g/ml) auxiliary materials are added to the ergothioneine-containing fermentation broth.

The present application also provides a composition comprising ergothioneine, hyaluronic acid or a salt thereof and trehalose. The composition has better antioxidant effect and anti-apoptotic effect. The inhibitory and scavenging effects on intracellular reactive oxygen species of the composition obtained by simultaneously using hyaluronic acid or a salt thereof and trehalose as auxiliary materials are significantly higher than that of single hyaluronic acid or a salt thereof or trehalose as auxiliary materials. Wherein, the hyaluronate is at least one selected from the group consisting of: sodium salt, potassium salt, magnesium salt, zinc salt, calcium salt or quaternary ammonium salt.

In a specific embodiment, in the composition, the mass ratio of ergothioneine, hyaluronic acid or a salt thereof to trehalose is 1:(20 to 1000):(1000 to 1980). For example, it can be 1:20:1000, 1:20:1500, 1:20:1980, 1:100:1000, 1:100:1500, 1:100:1980, 1:500:1000, 1:500:1500, 1:500:1980, 1:1000:1000, 1:1000:1500, 1:1000:1980. In parts by weight, ergothioneine is 1 part by weight, hyaluronic acid or a salt thereof is 20 to 1000 parts by weight, such as 20 parts by weight, 50 parts by weight, 100 parts by weight, 300 parts by weight, 500 parts by weight, 700 parts by weight parts, 1000 parts by weight, preferably 100 to 180 parts by weight. Trehalose is 1000 to 1980 parts by weight, such as 1000 parts by weight, 1100 parts by weight, 1200 parts by weight, 1300 parts by weight, 1500 parts by weight, 1700 parts by weight, 1800 parts by weight, 1980 parts by weight, preferably 1800 to 1900 parts by weight. In a specific embodiment, the molecular weight of the hyaluronic acid or a salt thereof in the composition is 3 KDa to 30 KDa, such as 3 KDa, 5 KDa, 10 KDa, 15 KDa, 20 KDa, 25 KDa, 30 KDa, preferably 3 KDa to 10 KDa.

The use of hyaluronic acid or a salt thereof and/or trehalose in the present application can significantly improve the stability of ergothioneine, and especially in the process of spray-drying ergothioneine fermentation broth, it can significantly alleviate the damage to ergothioneine caused by high temperature. When using a certain proportion of hyaluronic acid or a salt thereof to trehalose as auxiliary materials for spray-drying in the treatment of ergothioneine fermentation broth, the obtained composition containing ergothioneine, hyaluronic acid or a salt thereof and trehalose has excellent antioxidant and anti-apoptotic effects. Especially when the mass ratio of hyaluronic acid or a salt thereof to trehalose in the composition is 1:19 to 1:10, the effect of inhibiting and scavenging reactive oxygen species is the best.

The following examples of the present application are only used to illustrate the specific embodiments for realizing the present application, and these embodiments should not be construed as limiting the present application. Any other changes, modifications, substitutions, combinations and simplifications made without departing from the spirit and principle of the present application are regarded as equivalent substitution methods and fall within the protection scope of the present application.

EXAMPLES

The present application will be further described below in combination with the examples, and it should be understood that the examples are only used to further explain and illustrate the present application, and are not intended to limit the present application.

The experimental methods used in the following examples are conventional methods unless otherwise required.

The materials, reagents, etc. used in the following examples can be obtained from commercial sources unless otherwise specified.

Example 1 Optimization of the Preparation of Ergothioneine Composition (Fermentation by Matsutake)

Liquid seed medium: 3.0% (w/v) lactose, 2.0% (w/v) potato extract, 0.1% (w/v) dipotassium hydrogen phosphate, 0.1% (w/v) sodium sulfate, the rest is water, pH 4.0~4.5, sterilized at 121° C. for 20 min;

Fermentation medium: 3.0% (w/v) glucose, 2.0% (w/v) maltose, 1.0% (w/v) beef extract, 1.5% (w/v) tryptone, 0.06% (w/v)/v) sodium dihydrogen phosphate, 0.0003% (w/v) zinc chloride, 0.0005% (w/v) niacin, 0.0001% (w/v) vitamin $B_1$, the rest is water, pH 4.0~4.5, sterilized at 121° C. for 20 min.

Mycelial slant strains of matsutake (*Tricholoma matsutake*) CCTCC No: M 2020587 were inoculated into the liquid seed medium, and cultured for 25 days under the condition of 23° C. and 200 rpm for shaking to obtain the seed liquid of matsutake. The seed liquid was inoculated into the fermentation medium at an inoculum of 5% by volume, and cultured for 25 days under the condition of 23° C. and 200 rpm for shaking, and the precursor substances cysteine, methionine and betaine were supplemented on the 20th day of the culture, each at 5 mM, to obtain a fermentation broth. After the fermentation, the mycelium fermentation broth was homogenized at 8000 rpm for 30 min using a homogenizing and emulsifying machine. Then, by filtering through a 1.2 μm fine filter cardboard and sterilizing by filtering with a 0.22 μm polyethersulfone filter element, the ergothioneine-containing solution could be obtained.

5% (w/v, g/ml) maltodextrin, microcrystalline cellulose, 3 KDa sodium hyaluronate, 5 KDa sodium hyaluronate, 10 KDa sodium hyaluronate, 15 KDa sodium hyaluronate, 30 KDa sodium hyaluronate, 50 KDa sodium polyglutamate, fucose, mannitol, β-cyclodextrin, lactose, trehalose and dextrin were added into the fermentation broth separately, mixed well, and sprayed with a centrifugal spray dryer. The inlet air temperature used in the spray-drying was 180° C., and the outlet air temperature was 90° C. The obtained powder was the ergothioneine-containing composition. The results of the ergothioneine content in each composition are shown in Table 1.

TABLE 1

Ergothioneine contentobtained byusing different auxiliary materials during spraying

| Sample | Auxiliary material | Ergothioneine content in the composition |
|---|---|---|
| Sample C1 | Maltodextrin | 0.158% |
| Sample C2 | microcrystalline cellulose | 0.151% |
| Sample C3 | Sodium Hyaluronate (5 KDa) | 0.167% |
| Sample C4 | Sodium polyglutamate | 0.159% |
| Sample C5 | Fucose | 0.159% |
| Sample C6 | Mannitol | 0.158% |
| Sample C7 | β-cyclodextrin | 0.157% |
| Sample C8 | lactose | 0.155% |
| Sample C10 | dextrin | 0.154% |
| Sample C11 | Sodium Hyaluronate (3 KDa) | 0.168% |
| Sample C12 | Sodium Hyaluronate (10 KDa) | 0.169% |
| Sample C13 | Sodium Hyaluronate (15 KDa) | 0.165% |
| Sample C14 | Sodium Hyaluronate (30 KDa) | 0.167% |

Ergothioneine inevitably suffers some damage during high-temperature spraying. As can be seen from the results in Table 1, in the composition obtained by using sodium hyaluronate and trehalose as auxiliary materials, the content of ergothioneine is 0.167%, 0.168%, 0.169%, 0.165%, 0.167% and 0.168% respectively, which are significantly higher than that of the powders obtained from several other commonly used auxiliary materials for spraying. It shows that sodium hyaluronate and trehalose can significantly alleviate the damage to ergothioneine caused by high temperature compared with that of other auxiliary materials.

Example 2 Optimization of the Preparation of Ergothioneine Composition (Fermentation by *Hericium erinaceus*)

Liquid seed medium: 4.0% (w/v) sucrose, 1.5% (w/v) soybean cake powder, 0.2% (w/v) sodium dihydrogen phosphate, 0.1% (w/v) sodium sulfate, and the rest is water, pH 4.0 to 4.5, sterilized at 121° C. for 20 min;

Fermentation medium: 3.0% (w/v) glucose, 1.5% (w/v) beef extract, 0.05% (w/v) sodium dihydrogen phosphate, 0.03% (w/v) sodium sulfate, 0.0003% (w/v) zinc chloride, 0.0006% (w/v) niacin, 0.0001% (w/v) vitamin $B_1$, and the rest is water, pH 4.0 to 4.5, sterilized at 121° C. for 20 min.

Mycelial slant strains of *Hericium erinaceus* CCTCC No: M 2018567 were inoculated into the liquid seed medium, and cultured for 7 days under the condition of 23° C. and 200 rpm for shaking to obtain the seed liquid of *Hericium erinaceus*. The seed liquid is inoculated into the fermentation medium at an inoculum of 5% by volume, and cultured for 10 days under the condition of 23° C. and 200 rpm for shaking, wherein the precursor substances cysteine, methionine and betaine were supplemented on the 5th day of the culture, each at 5 mM, to obtain a fermentation broth. After the fermentation, the mycelium fermentation broth was homogenized at 8000 rpm for 30 min using a homogenizing and emulsifying machine. Then, by filtering through a 1.2 μm fine filter cardboard and sterilizing by filtering with a 0.22 μm polyethersulfone filter element, the ergothioneine-containing solution could be obtained. 5% (w/v, g/ml) maltodextrin, microcrystalline cellulose, 3 KDa sodium hyaluronate, 5 KDa sodium hyaluronate, 10 KDa sodium hyaluronate, 15 KDa sodium hyaluronate, 30 KDa sodium hyaluronate, 50 KDa sodium polyglutamate, fucose, mannitol, β-cyclodextrin, lactose, trehalose and dextrin were added into the fermentation broth separately, mixed well, and sprayed with a centrifugal spray dryer. The inlet air temperature used in the spray-drying was 180 C. and the outlet air temperature was 90° C. The obtained powder was the ergothioneine-containing composition. The results of the ergothioneine content in each composition are shown in Table 2.

TABLE 2

| Ergothioneine content obtained by using different auxiliary materials during spraying | | |
|---|---|---|
| Sample | Auxiliary material | Ergothioneine content in the composition |
| Sample D1 | Maltodextrin | 0.365% |
| Sample D2 | microcrystalline cellulose | 0.353% |
| Sample D3 | Sodium Hyaluronate (5 KDa) | 0.392% |
| Sample D4 | Sodium polyglutamate | 0.362% |
| Sample D5 | Fucose | 0.361% |
| Sample D6 | Mannitol | 0.364% |
| Sample D7 | β-cyclodextrin | 0.359% |
| Sample D8 | lactose | 0.355% |
| Sample D9 | trehalose | 0.395% |
| Sample D10 | dextrin | 0.360% |
| Sample D11 | Sodium Hyaluronate (3 KDa) | 0.394% |
| Sample D12 | Sodium Hyaluronate (10 KDa) | 0.394% |
| Sample D13 | Sodium Hyaluronate (15 KDa) | 0.395% |
| Sample D14 | Sodium Hyaluronate (30 KDa) | 0.392% |

As can be seen from the results in Table 2, using *Hericium erinaceus* for fermentation, in the composition obtained using sodium hyaluronate and trehalose as auxiliary materials, the content of ergothioneine is also significantly higher than that of the powder obtained by using several other commonly used spray auxiliary materials. It shows that sodium hyaluronate and trehalose can significantly alleviate the damage to ergothioneine caused by high temperature during spraying.

Example 3 Optimization of the Ratio of Hyaluronic Acid to Trehalose

It can be seen from the results of Example 1 and Example 2 that both sodium hyaluronate and trehalose have good stabilizing effects on ergothioneine. Among them, sodium hyaluronate has good moisturizing, anti-inflammatory and other effects, but the price is relatively high, therefore, in order to reduce costs, and at the same time obtain a composition with better moisturizing, anti-inflammatory and other effects, it was considered to use sodium hyaluronate (5 KDa) and trehalose with different ratios as auxiliary materials for spraying. Wherein, using the fermentation broth of Example 1, during the spray-drying of the fermentation broth, the mixture of sodium hyaluronate and trehalose were used as auxiliary materials, wherein the mass ratio of sodium hyaluronate to trehalose was adjusted from 1:99 to 50:50. Also with the addition amount of auxiliary materials at 5% (w/v, g/ml) of the fermentation broth, and using the same operation conditions of spray-drying as above, the content of ergothioneine in the obtained composition is shown in Table 3.

TABLE 3

| Sample | Mass ratio of sodium hyaluronateto trehalose | Ergothioneine content in the composition |
|---|---|---|
| Sample S1 | 1:99 | 0.168% |
| Sample S2 | 2:98 | 0.168% |
| Sample S3 | 3:97 | 0.169% |
| Sample S4 | 5:95 | 0.168% |
| Sample S5 | 10:90 | 0.167% |
| Sample S6 | 15:85 | 0.168% |
| Sample S7 | 20:80 | 0.167% |
| Sample S8 | 30:70 | 0.168% |
| Sample S9 | 50:50 | 0.167% |

It can be seen from the above table that the use of sodium hyaluronate and trehalose as auxiliary materials with a mass ratio of 1:99 to 50:50 can effectively alleviate the damage to ergothioneine caused by high temperature during spraying. However, when the molecular weight of sodium hyaluronate is greater than 10 KDa, the yield of the powder obtained by spraying is slightly reduced due to the large molecular weight and high viscosity, so the molecular weight of sodium hyaluronate is preferably 3 KDa to 10 KDa.

Example 4 Antioxidant Activity of the Composition

1. Effects on the Generation of Reactive Oxygen Species

Preparation of sample solution: the samples C3, C9, S1-9 prepared in the above-mentioned examples were prepared into 0.1% (w/v, g/ml) solutions with serum-free DMEM culture medium respectively, and the sample S4 was prepared into solutions at concentrations of 0.05% (w/v, g/ml), 0.1% (w/v, g/ml), 0.2% (w/v, g/ml), and 0.3% (w/v, g/ml), and sterilized by filtration through a 0.22 μm filter membrane.

(1) Active Oxygen Species Scavenging Test

Preparation of dichlorofluorescein diacetate (DCFH-DA) probe solution: DCFH-DA was diluted with PBS solution (0.1 M, pH 7.4) by adding 0.375 μL to 1 mL of PBS.

HaCaT cells in logarithmic growth phase were taken and inoculated into a 12-well culture plate at a density of $5\times10^4$ cells/mL, with 2 mL of cell suspension per well, and were placed in a carbon dioxide incubator at 37° C. and 5% $CO_2$ for 24 hours of conventional culture. They were operated in groups as follows:

(1) In the irradiation group, 1 mL of culture medium was discarded, covered with plastic wrap, irradiated with UVA at an intensity of 2000 $\mu W/cm^2$ for 2-3 h, and irradiated with UVB at an intensity of 700 $\mu W/cm^2$ for 7 min; after irradiation, the old culture solution was discarded and add 2 each sample solution was added, 2 mL in each well;

(2) In the damage model group, the operation was the same as that in the irradiation group. After irradiation, the old culture medium was discarded, and serum-free culture medium was added, 2 mL in each well;

(3) The normal control group was conventionally cultured, and the medium was replaced at the same time as that in the irradiation group, and serum-free culture medium was added, 2 mL in each well;

Then, after culturing for 16 hours, all the culture medium was discarded and they were washed twice with PBS. 1.5 mL of DCFH-DA solution was added to each well, and they were placed in a cell incubator and continued to incubate for 30 min, and mixed well every 5 min to make the probes bind fully. The probe solution was discarded, they were washed twice with serum-free medium, and 1 mL of serum-free medium was added to each well and incubated at 37° C. for 10 min. After washing once with PBS, cells were digested with trypsin, washed twice with PBS, resuspended in 300 μL PBS, and detected by flow cytometer using two channels.

Before loading on the machine, cells were filtered. Through FL1-H channel, 1000 cells were collected for each sample. According to the signal data acquired in channel 1 (FL1-H) (i.e., the fluorescence intensity or total fluorescence generated by DCF), the ROS scavenging rate was calculated. ROS scavenging was calculated by mean fluorescence intensity:

ROS scavenging rate %=(1−mean fluorescence intensity of experimental group/mean fluorescence intensity of control group)×100%

(2) Reactive Oxygen Species Inhibition Test

HaCaT cells in logarithmic growth phase were taken and inoculated in a 12-well culture plate at a density of $4\times10^4$ cells/mL, with 2 mL of cell suspension per well, and were placed in a carbon dioxide incubator at 37° C. and 5% $CO_2$ for 24 h of conventional culture.

The old culture medium was discarded, the sample solution was added to the experimental group, the serum-free culture medium was added to the normal control group, 2 mL each well, and the culture was continued for 24 hours before irradiation. The normal control group was covered with aluminum foil and without irradiation.

In the irradiation group, 1 mL of culture medium was discarded, covered with plastic wrap, UVA was irradiated at an intensity of 2000 $\mu W/cm^2$ for 1 h, UVB was irradiated at an intensity of 700 $\mu W/cm^2$ for 3 min, and the normal control group was not irradiated. The medium was discarded and they were washed twice with PBS. 1.5 mL of DCFH-DA was added to each well, and they were placed into a cell incubator and continued to incubate for 30 min, and mixed well every 5 min to make the probe bind fully. The probes were discarded, and they were washed twice with pre-warmed serum-free medium, and 1 mL of serum-free medium was added to each well and incubated at 37° C. for 10 min. After washing once with PBS, cells were digested with trypsin, washed twice with PBS, resuspended in 300 μL of PBS, and detected by flow cytometer using two channels (the cells need to be filtered before loading on the machine). Through FL1-H channel, 10,000 cells were collected for each sample. According to the signal data acquired in channel 1 (FL1-H) (i.e., the fluorescence intensity or total fluorescence generated by DCF), the ROS scavenging rate was calculated. ROS scavenging was calculated by mean fluorescence intensity: ROS inhibition rate %=(1−mean fluorescence intensity of experimental group/mean fluorescence intensity of control group)×100%

The obtained results of ROS scavenging rate and inhibition rate of each sample are shown in Table 4 and Table 5.

TABLE 4

Effects of samples at 0.1% concentrationon the generation of reactive oxygen species(ROS)

| Sample | C3 | C9 | S1 | S2 | S3 | S4 | S5 | S6 | S7 | S8 | S9 |
|---|---|---|---|---|---|---|---|---|---|---|---|
| ROS scavenging rate (%) | 18.35 | 19.22 | 25.33 | 24.97 | 29.05 | 32.04 | 32.47 | 29.56 | 25.03 | 24.89 | 25.17 |
| ROSinhibition rate (%) | 9.48 | 9.33 | 14.86 | 14.21 | 17.11 | 19.37 | 19.69 | 17.04 | 14.34 | 14.11 | 14.56 |

TABLE 5

Effects of different sample concentrations on the generation of reactive oxygen species(ROS)

| | Sample concentration | | | |
|---|---|---|---|---|
| | 0.05 | 0.1 | 0.2 | 0.3 |
| ROS scavenging rate (%) | 20.19 | 32.43 | 26.71 | 23.15 |
| ROS inhibition rate (%) | 10.01 | 19.28 | 16.71 | 17.45 |

From the results in Table 4, it can be seen that the ergothioneine composition obtained by the present application has a good antioxidant effect, and the inhibition and scavenging effects on intracellular reactive oxygen species of the composition obtained by simultaneously using hyaluronate and trehalose as auxiliary materials are significantly greater than that of the composition obtained by using single hyaluronate or trehalose as an auxiliary material, and when the addition ratio of hyaluronate to trehalose is 1:19 to 1:10, the inhibition and scavenging effects on reactive oxygen species are most obvious. It can be seen from the results in Table 5 that the sample S4 is in the concentration range of 0.01%, 0.05%, 0.1% and 0.2%, and ergothioneine has the strongest inhibition and scavenging effect on the intracellular reactive oxygen species caused by UV damage at the concentration of 0.1%. The inhibition and scavenging rate are 19.28% and 32.43%, respectively. At both lower and higher concentrations, the inhibition and scavenging efficacies decrease.

2. DPPH Free Radical Scavenging Test

The above-prepared sample S4 was dissolved in water to prepare solutions with final concentrations of 0.05% (w/v), 0.1% (w/v), 0.2% (w/v) and 0.3% (w/v) for use. 5.0 mL of 1,1-diphenyl-2-trinitrophenylhydrazine (DPPH) solution and 5.0 mL of sample solution of S5 with different concentrations were precisely measured, placed in test tubes with stoppers, and mixed well. An equal volume of 95% ethanol-water mixture was used for zero setting. It was placed at room temperature for 30 minutes, and the absorbance value of the solution was measured at 523 nm, with 3 repetitions for each concentration; another group was set up to precisely measure 5.0 mL of DPPH solution to mix with 5.0 mL of purified water, as a blank control, and the operation was the same as above. The calculation method is as follows:

ROS scavenging rate (%)=(1−absorbance value of sample/absorbance value of blank control)×100%

The obtained results are shown in Table 6.

TABLE 6

| Results of DPPH free radical scavenging activity of samples with different concentrations | | | | | | |
|---|---|---|---|---|---|---|
| Sample concentration (%) | 0.05 | 0.1 | 0.2 | 0.3 | 0.4 | 0.5 |
| DPPHDPPHfree radical scavenging rate (%) | 19.35 | 37.01 | 51.65 | 74.80 | 86.46 | 88.14 |

It can be seen from the results in Table 6 that with the increase of the concentration of the composition, the scavenging rate of DPPH free radicals also increases. When the concentration of the composition is 0.3%, the scavenging rate can reach 74.80%, and when the concentration is 0.5%, the scavenging rate reaches 88.14%.

Example 5 Evaluation of the Anti-Apoptotic Efficacy of the Composition

Preparation of sample solution: the sample S4 was prepared into solutions at concentrations of 0.1% (w/v), 0.3% (w/v) and 0.5% (w/v) with serum-free culture medium, respectively, and sterilized by filtration through a 0.22 μm filter membrane.

(1) the Repair Effect of the Test Sample on the Apoptosis Due to UVB Irradiation Plate: HaCaT cells in logarithmic growth phase were taken and digested with trypsin. Then the cell density was adjusted to $1\times10^6$ cells/mL, and the cells were inoculated in 6-well cell culture plate, with 2 mL of cell suspension per well, and placed in a carbon dioxide incubator at 37° C., 5% $CO_2$ for conventional culture overnight.

Irradiation: opening the lid of the 6-well plate, sealing the plate with plastic wrap, and irradiating HaCaT cells with 70 mJ/cm$^2$ UVB (400 μW 3 min). Test groups were shown in Table 7:

TABLE 7

| Grouping of the repair effect of test samples on apoptosis due to UVB irradiation | |
|---|---|
| Group | Treatment method |
| Normal group | Without irradiation, adding serum-free medium |
| Model group | After UVB irradiation, adding serum-free medium |
| Test group | After UVB irradiation, adding different concentrations of ergothioneine sample solutions |

Drug adding: after irradiation, the culture medium was discarded, 2 mL of sample solutions of different concentrations were added to each well of the test group, and the same amount of culture medium was added to the normal group and the model group, and they were placed in an incubator to continue culturing.

Detection: after culturing for 24 hours, cells in 6-well plates of each group were collected, and the old culture medium was pipetted into EP tubes. The cells were washed once with PBS, trypsin was added for digestion, and then the old culture medium was added to terminate the digestion. They were collected to the above EP tubes, centrifuged at 1000 rpm/min for 5 minutes, and the supernatant was discarded. After washing twice with pre-cooled PBS, the cells were resuspended with 1×Binding Buffer, the cell density was adjusted to $1\times10^6$ cells/mL, and 100 μL of the cell suspension was transferred to a new 1.5 mL EP tube. According to the kit instructions, 5 μL Annexin V-FITC and PI staining solution were added respectively, mixed gently, incubated at room temperature for 10 minutes in the dark, and detected by flow cytometry.

(2) Protective Effect of Test Sample on Apoptosis Due to UVB Irradiation

Plate: HaCaT cells in logarithmic growth phase were taken, and digested with trypsin. Then the cell density was adjusted to $1\times10^6$ cells/mL, and the cells were inoculated into 6-well cell culture plate, with 2 mL of cell suspension per well, and placed in a carbon dioxide incubator at 37° C., 5% $CO_2$ for conventional culture overnight.

Drug adding: the old culture medium was discarded, 2 mL of sample solutions of different concentrations were added to each well for the test group, and the same amount of culture medium was added to the normal group and the model group, and they were placed into the incubator to continue culturing.

Irradiation: opening the lid of the 6-well plate, sealing the plate with plastic wrap, and irradiating HaCaT cells with 70 mJ/cm$^2$ UVB (400 μW 3 min). Test groups were shown in Table 8:

TABLE 8

| Grouping of the protective effect of the test samples on apoptosis due to UVB irradiation | |
|---|---|
| Groups | Treatment method |
| Normal group | Adding serum-free medium, without irradiation |
| Model group | After adding serum-free medium, UVB irradiation |
| Test group | After adding different concentrations of ergothioneine sample solutions, UVB irradiation |

Detection: after culturing for 24 hours after irradiation, cells in 6-well plates of each group were collected, and the old culture medium was pipetted into EP tubes. The cells were washed once with PBS, trypsin was added for digestion, and then the old culture medium was added to terminate the digestion. They were collected and transferred to the above EP tubes and centrifuged at 1000 rpm/min for 5 minutes, and the supernatant was discarded. After washing twice with pre-cooled PBS, the cells were resuspended with 1×Binding Buffer, the cell density was adjusted to $1\times10^6$ cells/ml, and 100 μL of cell suspension were taken and transferred to a new 1.5 mL EP tube. According to the kit instructions, 5 μL Annexin V-FITC and PI staining solution were added respectively, mixed gently, incubated at room temperature for 10 minutes in the dark, and detected by flow cytometry.

In normal cells, phosphatidylserine (PS) is only distributed in the inner side of the lipid bilayer of the cell membrane, while in the early stage of apoptosis, the phosphatidylserine (PS) in the cell membrane is turned from the inside to the outside of the lipid membrane. Annexin V is a $Ca^{2+}$-dependent phospholipid-binding protein with a molecular weight of 35-36 kD. It has a high affinity for phosphatidylserine, so it can bind to the cell membrane of early apoptotic cells through phosphatidylserine exposed on the outside of the cell. Propidium iodide (PI) is a nucleic acid dye that cannot penetrate the complete cell membrane, but for cells in the middle and late stages of apoptosis and dead cells, PI can penetrate the cell membrane and stain the nucleus red. Therefore, the matched use of Annexin V and PI can distinguish cells in different apoptotic stages.

The results are shown in Table 9. No matter whether it was contacted with the sample before UV damage or contacted with the sample after UV irradiation damage, the inhibitory effect of sample S4 at a concentration of 0.1% is the strongest, and with the concentration further increases, the anti-apoptotic effect decreases

TABLE 9

Effects of S4 on the apoptosis of HaCaT cells due to UV damage

| | Sample concentration (%) | | | |
|---|---|---|---|---|
| | 0.05 | 0.1 | 0.2 | 0.3 |
| Apoptosis inhibition rate of protective effect (%) | 6.05 | 8.28 | 4.41 | 5.29 |
| Apoptosis inhibition rate of repair effect (%) | 21.31 | 34.22 | 27.63 | 19.81 |

The invention claimed is:

1. An additive for stabilizing ergothioneine, wherein the additive consists of hyaluronic acid or a salt thereof and trehalose, wherein the mass ratio of the hyaluronic acid or a salt thereof to trehalose is 1:99 to 50:50, and wherein the molecular weight of the hyaluronic acid or a salt thereof is 3 KDa to 10 KDa.

2. The additive according to claim 1, wherein the mass ratio of the hyaluronic acid or a salt thereof to trehalose is 1:19 to 1:10.

3. The additive according to claim 1, wherein the additive is used as an auxiliary material for spray-drying treatment of ergothioneine fermentation broth.

4. A composition, wherein the composition comprises ergothioneine and the additive according to claim 1.

5. A composition, wherein the composition comprises ergothioneine and the additive according to claim 2.

6. A composition, wherein the composition comprises ergothioneine and the additive according to claim 3.

7. A composition, wherein the composition comprises ergothioneine, hyaluronic acid or a salt thereof and trehalose, wherein in parts by weight, ergothioneine is 1 part by weight, hyaluronic acid or a salt thereof is 20 to 1000 parts by weight, and trehalose is 1000 to 1980 parts by weight, and wherein the molecular weight of the hyaluronic acid or a salt thereof is 3 KDa to 10 KDa.

8. The composition according to claim 7, wherein in parts by weight, ergothioneine is 1 part by weight, hyaluronic acid or a salt thereof is 100 to 180 parts by weight, and trehalose is 1800 to 1900 parts by weight.

9. The composition according to claim 7, wherein the composition has an antioxidant effect.

10. A method for improving the thermostability of ergothioneine, comprising contacting the ergothioneine with hyaluronic acid or a salt thereof and trehalose to improve the thermostability of the ergothioneine, wherein the mass ratio of the hyaluronic acid or a salt thereof to trehalose is 1:99 to 50:50, and wherein the molecular weight of the hyaluronic acid or a salt thereof is 3 KDa to 30 KDa 10 KDa.

* * * * *